United States Patent
Khallaghi et al.

(10) Patent No.: US 10,909,677 B2
(45) Date of Patent: Feb. 2, 2021

(54) SYSTEMS AND METHODS FOR PERFORMING A MEASUREMENT ON AN ULTRASOUND IMAGE DISPLAYED ON A TOUCHSCREEN DEVICE

(71) Applicant: Clarius Mobile Health Corp., Burnaby (CA)

(72) Inventors: Siavash Khallaghi, Vancouver (CA); Benjamin Eric Kerby, Richmond (CA)

(73) Assignee: Clarius Mobile Health Corp., Vancouver (CA)

( * ) Notice: Subject to any disclaimer, the term of this patent is extended or adjusted under 35 U.S.C. 154(b) by 122 days.

(21) Appl. No.: 16/276,542

(22) Filed: Feb. 14, 2019

(65) Prior Publication Data
US 2020/0265577 A1 Aug. 20, 2020

(51) Int. Cl.
*G06T 7/00* (2017.01)
*G06T 7/155* (2017.01)
*G06T 7/149* (2017.01)

(52) U.S. Cl.
CPC ............ *G06T 7/0012* (2013.01); *G06T 7/149* (2017.01); *G06T 7/155* (2017.01); *G06T 2207/20116* (2013.01); *G06T 2207/20161* (2013.01)

(58) Field of Classification Search
CPC ....... G06T 7/0012; G06T 7/155; G06T 7/149; G06T 2207/20161; G06T 2207/20116
See application file for complete search history.

(56) References Cited

U.S. PATENT DOCUMENTS

| | | | |
|---|---|---|---|
| 6,385,332 B1* | 5/2002 | Zahalka | G06T 7/0012 128/922 |
| 6,785,409 B1 | 8/2004 | Suri | |
| 6,792,071 B2 | 9/2004 | Dewaele | |
| 9,014,441 B2* | 4/2015 | Truyen | A61B 5/1072 382/128 |

(Continued)

FOREIGN PATENT DOCUMENTS

| | | |
|---|---|---|
| WO | 2008072157 | 6/2008 |
| WO | 2012140147 | 10/2012 |

OTHER PUBLICATIONS

Automatic Active Contour-Based Segmentation and Classification of Carotid Artery Ultrasound Images (Year: 2013).*
CT Colonography: Automated Measurement of Colonic Polyps Compared with Manual TechniquesHuman in Vitro Study (Year: 2007).*

(Continued)

*Primary Examiner* — Nizar N Sivji
(74) *Attorney, Agent, or Firm* — Julian Ho

(57) ABSTRACT

The present embodiments relate generally to systems and methods for performing a measurement on an ultrasound image displayed on a touchscreen device. The method may include: receiving, via the touchscreen device, first input coordinates corresponding to a point on the ultrasound image; using the first input coordinates as a seed for performing a contour identification process on the ultrasound image, wherein the contour identification process performs contour evolution using morphological operators to iteratively dilate from the first input coordinates; upon identification of a contour from the contour identification process, placing measurement calipers on the identified contour; and storing a value identified by the measurement calipers as the measurement.

20 Claims, 6 Drawing Sheets
(2 of 6 Drawing Sheet(s) Filed in Color)

(56) References Cited

U.S. PATENT DOCUMENTS

| | | | |
|---|---|---|---|
| 2007/0081705 A1* | 4/2007 | Carneiro | G06K 9/6226 |
| | | | 382/128 |
| 2008/0159606 A1* | 7/2008 | Suri | G06T 7/149 |
| | | | 382/128 |
| 2008/0317314 A1 | 12/2008 | Schwartz et al. | |
| 2016/0085328 A1* | 3/2016 | Lee | G06F 3/04845 |
| | | | 345/173 |
| 2016/0275678 A1* | 9/2016 | Onal | G06K 9/4642 |
| 2017/0124700 A1* | 5/2017 | Sarojam | A61B 8/46 |
| 2017/0164924 A1 | 6/2017 | Urabe et al. | |
| 2019/0148011 A1* | 5/2019 | Rao | A61B 8/5292 |
| | | | 600/437 |
| 2020/0113544 A1* | 4/2020 | Huepf | A61B 8/463 |

OTHER PUBLICATIONS

Automatic segmentation of intravascular ultrasound images: A texture-based Approach (Year: 1997).*

Fetal Abdominal Contour Extraction and Measurement in Ultrasound Images (Year: 2007).*

Polyps: Linear and Volumetric measurement at CT Colonography (Year: 2006).*

Segmentation and Size Measurement of Polyps in CT Colonography (Year: 2005).*

Yazdi, B. et al., Optimal caliper placement: manual vs automated methods, May 13, 2013, Ultrasound in Obstetrics & Gynecology, vol. 43, Issue 2.

* cited by examiner

SYSTEMS AND METHODS FOR PERFORMING A MEASUREMENT ON AN ULTRASOUND IMAGE DISPLAYED ON A TOUCHSCREEN DEVICE

FIELD

The present disclosure relates generally to ultrasound imaging, and in particular, systems and methods for performing a measurement on an ultrasound image displayed on a touchscreen device.

BACKGROUND

Medical diagnostic ultrasound imaging systems are becoming increasingly accessible. Some modern ultrasound medical imaging systems connect to off-the-shelf display computing devices such as those running iOS™ or Android™ operating systems. As compared to traditional ultrasound systems that have keyboards, a trackball or other physical input controls, off-the-shelf display computing devices typically receive input via touchscreens. While the use of touchscreen input may allow for a more familiar user interface similar to what is used on consumer devices, it may be difficult to be as precise using touchscreen input versus the physical controls of traditional ultrasound systems.

One area where this lack of precision may present a challenge is performing measurements on ultrasound images. Traditional manual approaches to caliper placement involve placing a first edge of the caliper on one side of the imaged structure to be measured, and then placing the second edge of the caliper on an opposing side of the imaged structure to be measured. Using a touchscreen to precisely place the edges of the calipers may be difficult since a fingertip of an ultrasound operator may typically be larger than that of the arrowhead of a cursor manipulated by manual controls (e.g., a trackball). These challenges may be even more pronounced in instances where the ultrasound operator is wearing protective gloves as they have less tactile feedback about finger placement.

Additionally, the screen size of off-the-shelf display computing devices vary greatly. In certain instances, measurements may be performed on tablet-sized computing devices with larger displays, and distances between points for caliper placement may be easily positioned. However, in certain other instances, the off-the-shelf display computing devices may also be smartphones with smaller display sizes. In these instances, a fingertip may have less pinpoint accuracy and it may be difficult to perform a measurement if the distance that is desired to be measured is small. For example, it may be difficult to place the two edges of a caliper on an ultrasound image because the two points are displayed close together on a smaller display.

Some traditional attempts at addressing these challenges include using measurement tools to automatically place calipers. However, these automatic tools rely on image analysis techniques that may not be accurate, and thus, may result in incorrect caliper placements. For example, some of these image analysis tools include contour identification techniques (e.g., an active contour model or "snakes" algorithm) that attempt to identify a structure within an ultrasound image. However, these algorithms typically require complex mathematical operations such as solving of differential equations that are computationally intensive. This may make them difficult to perform on mobile devices that have limited processing capabilities and battery power.

There is thus a need for improved ultrasound systems and methods for performing a measurement of an ultrasound image displayed on a touchscreen device. The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Non-limiting examples of various embodiments of the present disclosure will next be described in relation to the drawings, in which.

Figure 1:
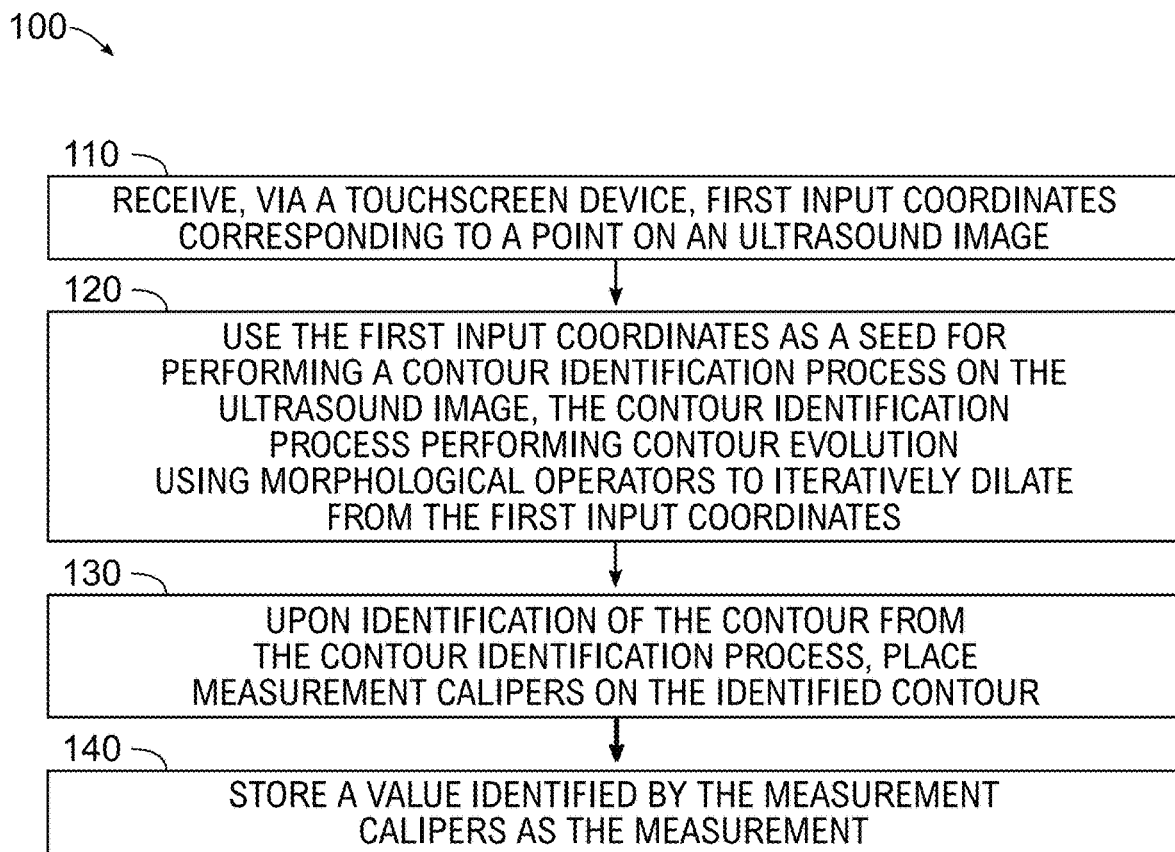
FIG. 1 is a flowchart diagram showing steps of a method of performing a measurement on an ultrasound image displayed on a touchscreen device, in accordance with at least one embodiment of the present invention.

Unless otherwise specifically noted, articles depicted in the drawings are not necessarily drawn to scale.

DETAILED DESCRIPTION

In a first broad aspect of the present disclosure, there is provided a method for performing a measurement on an ultrasound image displayed on a touchscreen device, the method including: receiving, via the touchscreen device, first input coordinates corresponding to a point on the ultrasound image; using the first input coordinates as a seed for performing a contour identification process on the ultrasound image, wherein the contour identification process performs contour evolution using morphological operators to iteratively dilate from the first input coordinates; upon identification of a contour from the contour identification process, placing measurement calipers on the identified contour; and storing a value identified by the measurement calipers as the measurement.

In some embodiments, prior to the storing of the value identified by the measurement calipers, the method further includes: receiving, via the touchscreen device, second input coordinates on the ultrasound image, wherein the second input coordinates adjust at least one side of the measurement calipers displayed on the identified contour.

In some embodiments, when placing the calipers on the identified contour, the method further includes: determining an axis of the identified contour; extending a length of the axis so that ends of the length overlap with contour; and placing the calipers on the ends of the length.

In some embodiments, principal component analysis is used to determine the axis of the identified contour, and the axis is a major axis or a minor axis identified by the principal component analysis.

In some embodiments, the contour identification process is initialized with a convergence parameter, and the method further includes: executing the contour identification process until the convergence parameter is achieved, to identify the contour from the contour identification process.

In some embodiments, executing the contour identification process until the convergence parameter is achieved includes: for a predetermined number of past iterations of the contour identification process, determining a mean and a variance of the contour data for the predetermined number of past iterations; determining if the variance of the contour data relative to the mean of the contour data is less than a threshold; and if the variance of the contour data relative to the mean is determined to be less than the threshold, the convergence parameter determined to be achieved.

In some embodiments, the predetermined number of past iterations is at least 7.

In some embodiments, each past iteration of the contour identification process includes a levelset, and the determining the mean and the variance of the contour data for the predetermined number of past iterations further includes: for each levelset, converting the levelset to a vector by serializing the two-dimensional data of the levelset; calculating a mean vector for the converted levelsets, to determine the mean of the contour data for the predetermined number of past iterations; and calculating the trace of the covariance of the converted levelsets, to determine the variance of the contour data for the predetermined number of past iterations.

In some embodiments, the determining if the variance of the contour data relative to the mean of the contour data is less than the threshold includes dividing the trace of the covariance of the converted levelsets by the norm of the mean vector. In some embodiments, the threshold is between 3 and 20 percent.

In some embodiments, after the convergence parameter is achieved, the method further includes: displaying a user interface control on the touchscreen device that, when activated, adjusts the identified contour to contract the contour or further dilate the contour.

In some embodiments, the convergence parameter includes a maximum number of iterations, and the convergence parameter is achieved when the contour identification process is executed for the maximum number of iterations.

In another broad aspect of the present disclosure, there is provided a touchscreen device capable of communicating with an ultrasound acquisition unit, the touchscreen device includes: a processor; and a memory storing instructions for execution by the processor, the instructions for performing a measurement on an ultrasound image displayed on a touchscreen device, wherein when the instructions are executed by the processor, the processor is configured to: receive, via the touchscreen device, first input coordinates corresponding to a point on the ultrasound image; use the first input coordinates as a seed for performing a contour identification process on the ultrasound image, wherein the contour identification process performs contour evolution using morphological operators to iteratively dilate from the first input coordinates; upon identification of a contour from the contour identification process, place measurement calipers on the identified contour; and store a value identified by the measurement calipers as the measurement.

In some embodiments, when placing the calipers on the identified contour, the processor is further configured to: determine an axis of the identified contour; extend a length of the axis so that ends of the length overlap with contour; and place the calipers on the ends of the length.

In some embodiments, the contour identification process is initialized with a convergence parameter, and the processor is further configured to: execute the contour identification process until the convergence parameter is achieved, to identify the contour from the contour identification process.

In some embodiments, when executing the contour identification process until the convergence parameter is achieved, the processor is further configured to: for a predetermined number of past iterations of the contour identification process, determine a mean and a variance of the contour data for the predetermined number of past iterations; determine if the variance of the contour data relative to the mean of the contour data is less than a threshold; and if the variance of the contour data relative to the mean is determined to be less than the threshold, the convergence parameter determined to be achieved.

In some embodiments, each past iteration of the contour identification process includes a levelset, and wherein when determining the mean and the variance of the contour data for the predetermined number of past iterations, the processor is further configured to: for each levelset, convert the levelset to a vector by serializing the two-dimensional data of the levelset; calculate a mean vector for the converted levelsets, to determine the mean of the contour data for the predetermined number of past iterations; and calculate the trace of the covariance of the converted levelsets, to determine the variance of the contour data for the predetermined number of past iterations.

In some embodiments, when determining if the variance of the contour data relative to the mean of the contour data is less than the threshold, the processor is further configured to divide the trace of the covariance of the converted levelsets by the norm of the mean vector.

In some embodiments, after the convergence parameter is achieved, the processor is further configured to: display a user interface control on the touchscreen device that, when activated, adjusts the identified contour to contract the contour or further dilate the contour.

In another broad aspect of the present disclosure, there is provided a computer readable medium storing instructions for performing a measurement on an ultrasound image displayed on a touchscreen device, the instructions for execution by a processor of a touchscreen device, wherein when the instructions are executed by the processor, the processor is configured to: receive first input coordinates corresponding to a point on the ultrasound image; use the first input coordinates as a seed for performing a contour identification process on the ultrasound image, wherein the contour identification process performs contour evolution using morphological operators to iteratively dilate from the first input coordinates; upon identification of a contour from the contour identification process, place measurement calipers on the identified contour; and store a value identified by the measurement calipers as the measurement.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

Referring to FIG. 1, shown there generally as 100 is a flowchart diagram showing steps of a method of performing a measurement on an ultrasound image displayed on a touchscreen device, in accordance with at least one embodiment of the present invention. The various acts of FIG. 1 may generally be performed on a multi-use touchscreen display device that is operatively connected to an ultrasound scanner. In discussing the method of FIG. 1, reference will simultaneously be made to FIGS. 2A-2B, which illustrates generally as 200 and 200' a series of images resulting from performing acts of the method of FIG. 1 on an ultrasound image, in accordance with at least one embodiment.

Figure 2A:
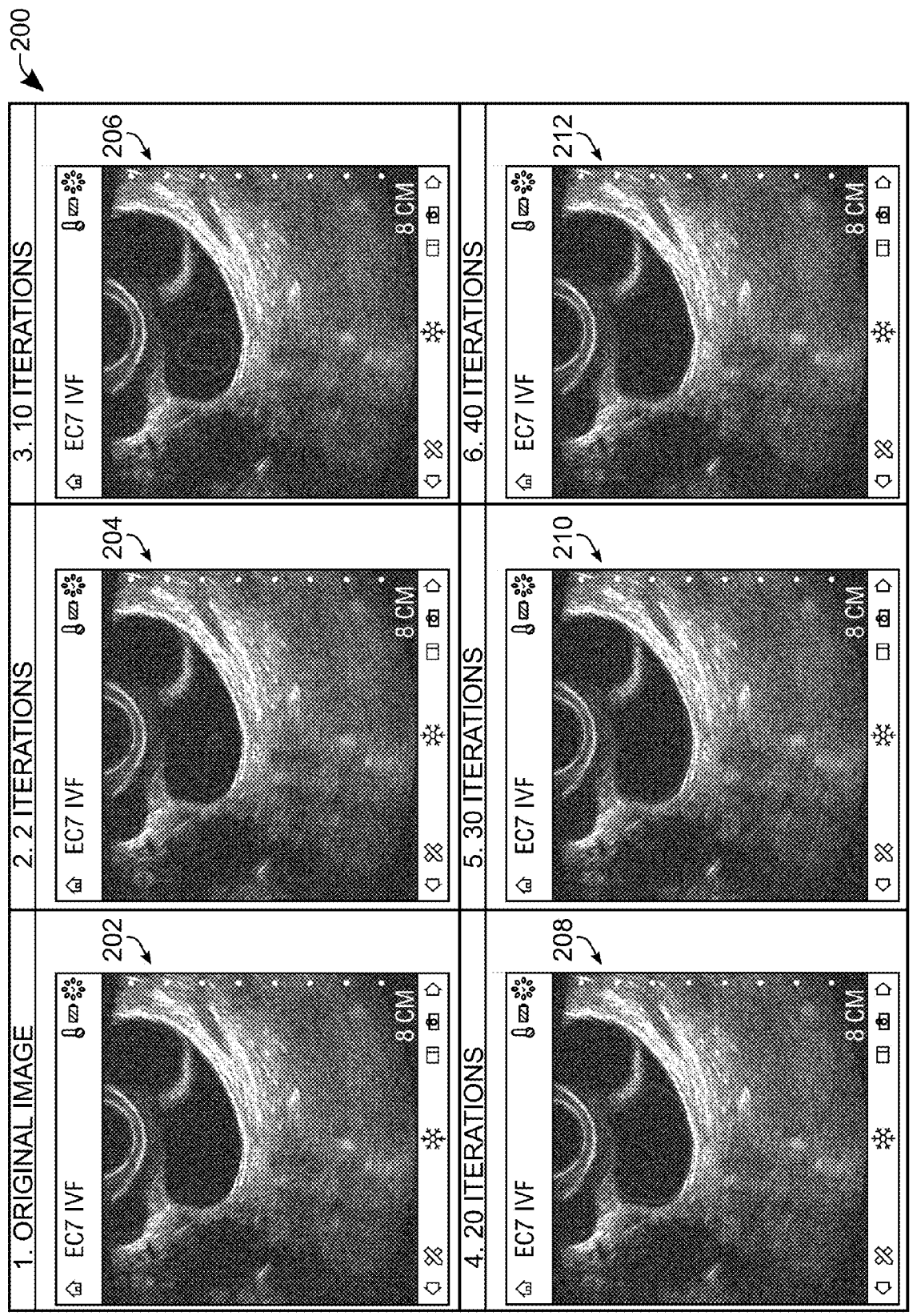
FIGS. 2A-2B are a series of images showing the result of performing acts of the present methods on an example ultrasound image, in accordance with at least one embodiment of the present invention.
Figure 2B:
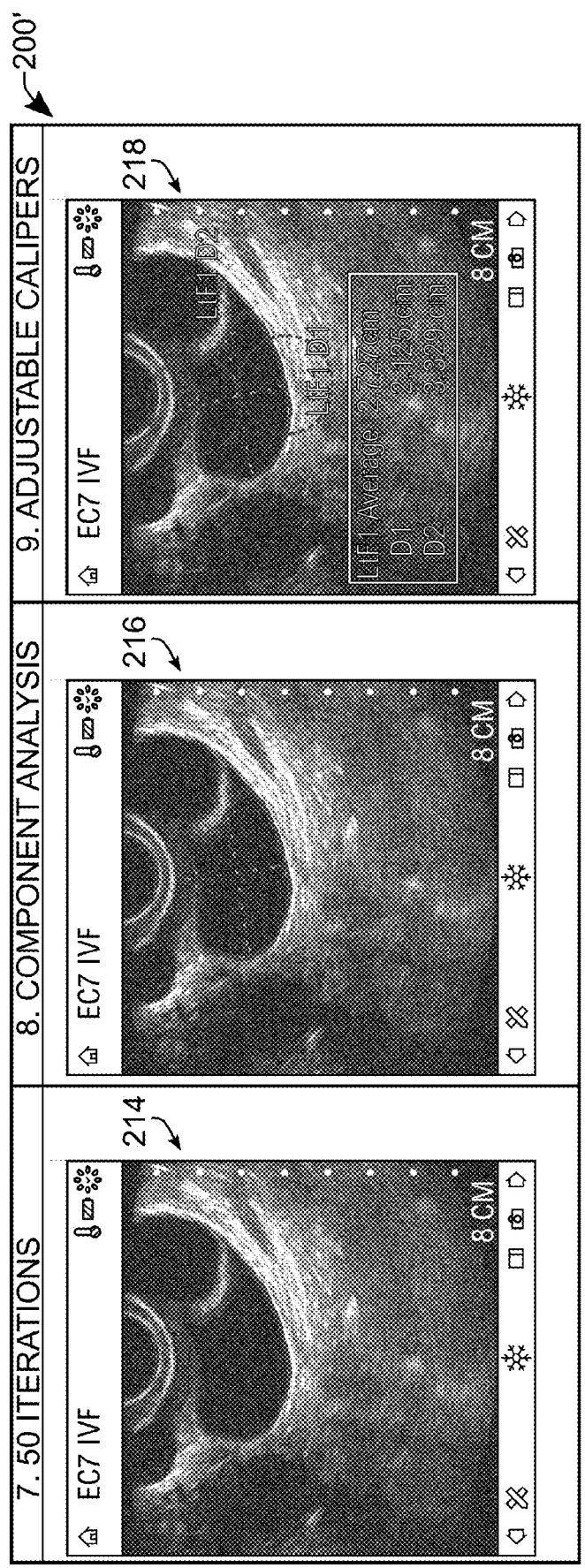

FIGS. 2A-2B show the application of the method of FIG. 1 on an example ultrasound image of an ovarian follicle. For example, during female fertility treatment, monitoring the size and/or count of ovarian follicles may be repeatedly performed to predict the best timing for ovulation and quantity of eggs that will ovulate, which, in turn, may help predict the success of fertility treatment. These types of ultrasound examinations may be performed using an endocavity ultrasound scanner (also called a transvaginal ultrasound scanner). An ultrasound scanner may also generally be called an ultrasound probe herein. While the methods of the present disclosure are described with respect to an ultrasound image of a follicle, it will be understood that the present methods may be performed on ultrasound images of other features too, so long as they have similar contrast with the background and the associated contours can be identified and measured. For example, the methods described herein may also be performed on other types of ultrasound images, such as ultrasound images of bladders, carotid cross-section, nerve bundles, or the like. Additionally or alternatively, the methods described herein may also be used for organ detection or abnormality detection during ultrasound imaging.

FIGS. 2A-2B illustrate a series of nine (9) frames, each containing a screenshot of an example user interface for an ultrasound imaging system that has captured an image of an ovarian follicle. The sequence of frames is labeled through '1' to '9' to show the result after successive acts of the methods described herein. The example user interface is for an ultrasound imaging scanner that can connect wirelessly to a multi-use display device (e.g., an electronic display unit 402 described in FIG. 4 below). In various embodiments, the device may be a smartphone or a tablet computer. This multi-use display device may also be referred to as a "touchscreen device" herein.

Referring briefly to frame '1' in FIG. 2A, in the top left-hand corner of the example user interface are the names of the scanner (e.g., "EC7") and a preset that may be used with the scanner (e.g., "IVF" for in vitro fertilization). On the top right-hand corner of the example user interface are icons for temperature, battery life, and connectivity. On the bottom of the example user interface are various controls. For example, these controls may be for navigating the user interface, or freezing a live ultrasound image feed (e.g., a 'snowflake' button in the bottom middle of the user interface for freezing the image). As shown, a frozen ultrasound image 202 of depth '8 cm' may be shown in the example user interface screenshot.

Referring back to FIG. 1, at act 110, the method may first begin by receiving, via the touchscreen device, first input coordinates corresponding to a point on the ultrasound image. For example, once the image is frozen, it may be desirable for an ultrasound operator to perform measurements on the imaged follicle as part of their assessment. Referring simultaneously to frame '1' of FIG. 2A, the large dark oblong shape near the top of the image may generally be visually identified by an ultrasound operator as the follicle. Act 110 may thus involve the touchscreen device receiving a touch input on the touchscreen device identifying that shape.

At act 120, using the first input coordinates as a seed for performing a contour identification process on the ultrasound image, the contour identification process may perform contour evolution using morphological operators to iteratively dilate from the first input coordinates.

Some traditional ultrasound systems may use image segmentation algorithms to automatically identify structures in ultrasound images. An example of such a traditional approach is to use an active contours model (also called a "snakes" algorithm) to delineate the outline of the oblong shape visually identified by the ultrasound operator. However, using the active contours model algorithm requires complex mathematical calculations involving the solving of partial differential equations. This is a computationally intensive process. While performing this type of process on a traditional cart-based ultrasound system with high computational and power capacity may not be a problem, executing this type of algorithms on a touchscreen device that connects to an ultra-portable ultrasound scanner may be more difficult. This is because the touchscreen device may be limited in processing ability and battery power; such that executing these types of traditional algorithms on a touchscreen device may result in lower responsiveness in the user interface of the ultrasound application executing on the touchscreen device.

Instead of using a traditional active contours model algorithm, the present embodiments may use a contour identification process that uses morphological operators. For example, to perform morphological processing on an image, an image may first be thresholded to generate a binary image. Then, a structuring element (for example, a small binary configuration of pixels that could be in the shape of a cross or a square) may be positioned at all possible locations of the binary image, to generate a secondary binary image. As each structuring element is positioned over the first binary image, how the structuring element relates to the underlying pixels of the first binary image impacts whether a pixel location is set to '1' or '0' in the secondary binary image.

For example, two common morphological operations are "erosion" and "dilation". In erosion, as the structuring element is positioned over the possible locations of the first binary image, it is required that all the '1' pixels in the first binary image "fit" into the structuring element for the corresponding pixel locations on the second image to be set to '1'. On the edges of any structures appearing on the first binary image, it will generally not be possible to meet this requirement because there will be a combination of '1's and '0's in the structuring element. This will result in some of those pixels that were set to '1' in the first binary image being set to '0' in the second binary image. In this manner, this operation results in a layer of pixels being "eroded" away in the second binary image.

In dilation, as the structuring element is positioned over the possible locations of the first binary image, it is only required that the structuring element "hit" any of the '1' pixels (e.g., that at least one of the pixels in the structuring element is a '1') for the corresponding pixel locations on the second image be set to '1'. On the edges of any structure appearing in the first binary image, there will again generally be a combination of '1's and '0's in the structuring element. However, unlike erosion, the requirement for the structuring element to "hit" a '1' pixel will be met. This will result in some of those pixels that were set to '0' in the first binary image be changed to a '1' in the second binary image. In this manner, this operation results in a layer of pixels being added, and thus the structure in the first binary image is "dilated" in the second binary image.

These types of morphological operators can be used in a contour identification process. For example, a morphological snakes algorithm is similar to the traditional active contours model or "snakes" algorithm, except that morphological operators (e.g., dilation or erosion) are used to grow or shrink the contour. Since morphological operators operate generally on binary images, operations can be performed over a binary array instead of over a floating point array (as would be the case if a traditional active contours model or "snakes" process is used). Thus, using a contour identification process that uses morphological operators may be considered less computationally intensive, and such processes may be particularly suitable for execution with ultrasound scanners that connect to mobile touchscreen devices that generally have lower computational capabilities and operate on battery power.

Referring still to FIG. 1, at act 130, upon identification of a contour from the contour identification process, the method may involve placing measurement calipers on the identified contour. Referring simultaneously briefly to FIG. 2B, an example ultrasound user interface is shown at frame '8' on ultrasound image 216, where the calipers are shown in green.

At act 140 of FIG. 1, a value identified by the measurement calipers as the measurement. For example, referring simultaneously to frame '9' of FIG. 2B, a number of the measurements (shown as an overlay in the white box) are illustrated. In the illustrated example, two measurements are shown for each of the two calipers: 'D1' with a measurement of '2.125 cm' and 'D2' with '3.329 cm'.

Figure 3A:
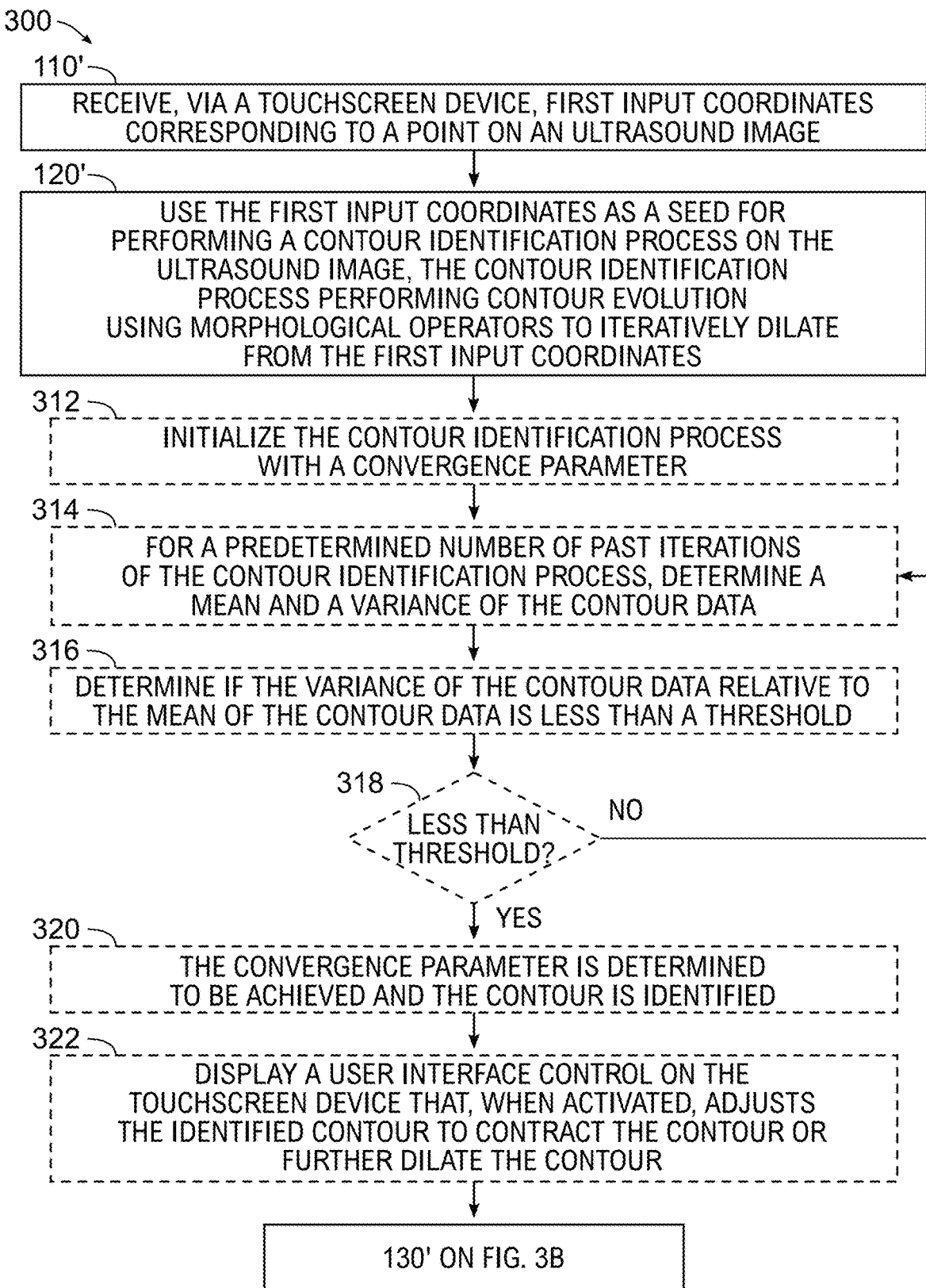
FIGS. 3A-3B is a flowchart diagram showing steps of a method of performing a measurement on an ultrasound image displayed on a touchscreen device, in accordance with at least one embodiment of the present invention.
Figure 3B:
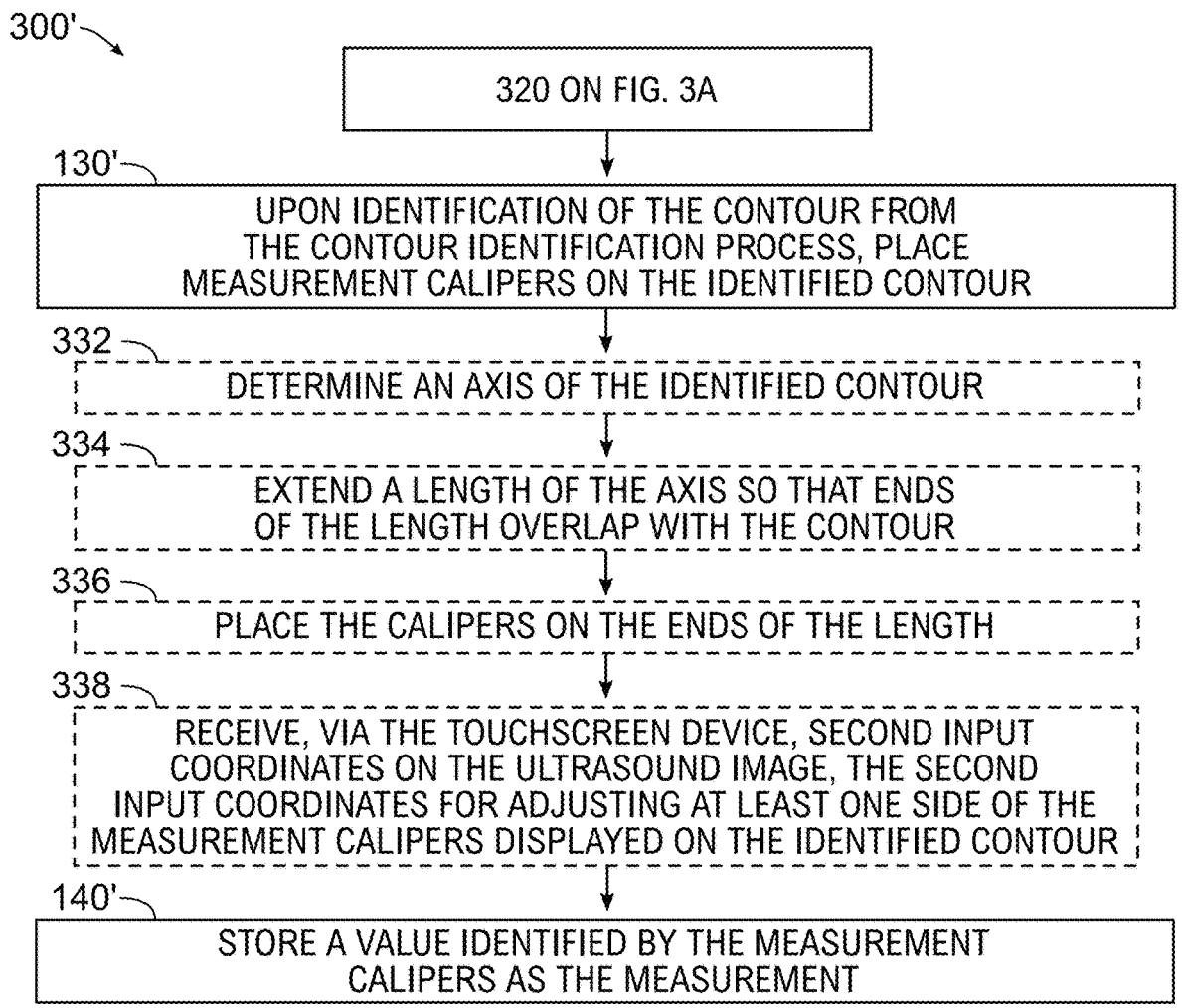

Referring to FIGS. 3A-3B, shown there generally as 300-300' is a flowchart diagram for steps of a method of performing a measurement on an ultrasound image displayed on a touchscreen device, in accordance with at least one embodiment of the present invention. The various acts of FIGS. 3A-3B may generally be performed on a multi-use touchscreen display device that is operatively connected to an ultrasound scanner. Some acts of the method 300-300' may be analogous to the acts of the method 100 of FIG. 1. In FIG. 3, certain example acts that may optionally be performed are shown in dotted outline.

As discussed below, some of the acts discussed in FIG. 3 may also generally correspond to images shown in FIGS. 2A and 2B. However, it will be understood that the method 300-300' of FIGS. 3A-3B as illustrated and discussed herein is only one example embodiment of many different embodiments of the present invention. While some of the frames of FIGS. 2A-2B were referenced above with respect to the method of FIG. 1, a discussion of all the various frames shown will now be discussed with respect to the method shown in FIGS. 3A-3B. The various frames in FIGS. 2A-2B generally show the progression of the contour identified by the contour identification process is at various stages of dilation. The contour is shown in the red color in these various frames.

At act 110', the method involves receiving, via the touchscreen device, first input coordinates corresponding to a point on the ultrasound image. This act may be performed in a manner similar to act 110 of FIG. 1 discussed above. Referring simultaneously to FIG. 2A, in frame '1', an original ultrasound image 202 is shown. For act 110' of FIG. 3A, the user interface may receive input identifying a point on the ultrasound image where the follicle is generally viewable. These first input coordinates generally correspond to location of the red shape is in the ultrasound image 204 in frame '2' of FIG. 2A.

At act 120', a next act may involve using the first input coordinates as a seed for performing a contour identification process on the ultrasound image, with the contour identification process performing contour evolution using morphological operators to iteratively dilate from the first input coordinates. Referring again simultaneously to FIG. 2A, in frame '2', the ultrasound image 204 shows the initial stages of the contour at two (2) iterations. At frame '3', the contour identification process at ten (10) iterations is shown, and it can be seen that the contour has dilated outward toward the edges of the underlying follicle structure (which appears as a black, generally oblong shape on the ultrasound image 206).

Referring still to FIG. 2A, at frame '4', the contour identification process is shown at twenty (20) iterations, and it can be seen on the ultrasound image 208 that, compared to the contour shown in frame '3', the contour continued to dilate. While the contour in frame '4' has dilated to more closely match the edges of the underlying structure, there are still gaps between the contour at this stage and the underlying structure. For example, the left edge of the contour has not fully reached the left edge of the underlying structure. Also, the bottom right corner of the contour has not fully extended into the elongated bottom right portion of the structure. Further, there is a dark portion in the top right corner of the underlying structure that the contour has not dilated into. As the contour identification process continues to execute to thirty (30), forty (40), and fifty (50) iterations in frames '5', '6', and '7', it can be seen in the ultrasound images 210, 212, and 214 respectively that these various gaps continue to get filled out.

In the illustrated example of FIGS. 2A-2B, over frames '5' to '7', it can be seen that while there have been some changes to the identified contour over the course over twenty (20) iterations, these changes may not change the shape of the contour in a way that significantly impacts the later caliper placement. It may thus have potentially been possible to stop the execution of the contour identification process sooner.

It can thus be seen that one of the challenges that arise when executing a contour identification process is when to stop executing the contour identification process and consider the contour to be identified. Referring back to FIG. 3A, in an example embodiment, as a part of performing the contour identification process of act 120', the method may perform one or more of acts 312-320 to help address this challenge.

At act 312, the contour identification process may be initialized with a convergence parameter. The contour identification process may then be executed only until the convergence parameter is achieved.

In some embodiments, the convergence parameter may be a maximum number of iterations and the convergence parameter is achieved when the contour identification process is executed for the maximum number of iterations. While using a maximum number of iterations as a convergence parameter may work, it may be difficult to select an optimal maximum number. For example, if the maximum number of iterations is set too low, then the resulting contour may not fully expand to reach the full shape of the underlying structure desired to be identified. This may result in the subsequent caliper placement not being accurate (and thus ultimately not useful for the ultrasound operator). For example, referring again simultaneously to FIG. 2A, if the maximum number of iterations were only set to twenty (20) iterations, the contour identification process may stop where the contour is shown in frame '4' and the left and right edge of the contour may not fully extend to the edges of the underlying structure desired to be identified.

On the other hand, to prevent premature termination of the contour identification process, it may be possible to err on the side of a higher number of maximum iterations—e.g., ten thousand (10,000) iterations. While this may reduce the likelihood of an identified contour being not fully dilated, it is possible that with such configuration, the contour identification has converged much sooner. In such case, many iterations of the contour identification process are superfluous and unnecessary. While such extraneous execution of the contour identification process may be acceptable on larger ultrasound imaging systems with high computational processing capabilities and unlimited electrical power, such a configuration would be inefficient if executed on a mobile touchscreen device that connects to a portable ultrasound scanner. For example, such configuration may reduce responsiveness of the user interface while the unnecessary iterations are being executed, and/or waste battery power of the touchscreen device.

In another example embodiment, the convergence parameter may be configured differently. For example, executing the contour identification process until the convergence parameter is achieved may include executing acts of 314-320 shown in FIG. 3A.

At act 314, for a predetermined number of past iterations of the contour identification process, a mean and a variance of the contour data for the predetermined number of past iterations may be determined.

In some embodiments, the contour identification process may be performed using a levelset function approach. As will be understood by persons skilled in the art, a levelset function approach to contour identification conceptually involves considering each evolution of the contour during the identification process as a plane that intersects a three-dimensional surface. Where each horizontal "level" intersects the three-dimensional surface may be considered the contour at a given iteration.

The levelset function can be defined in various ways, depending on the implementation. For example, in an example embodiment, a signed distance function may be used as the levelset function in a morphological snakes algorithm, where pixel locations on the contour desired to be identified have a value of '0', pixel locations inside the contour have a negative value, and pixel locations outside the contour have a positive value. Additionally or alternatively, the levelset function can be defined in a way where pixel locations are considered '0' outside the contour and '1' inside the contour.

Referring still to FIG. 3A, in an embodiment where each iteration corresponds to a levelset of an evolving levelset function, the determination of the mean and variance of the contour data at act 314 may involve determining the mean and variance for a past number of levelsets. For example, in an embodiment where the levelset function is defined in a way that considers pixel locations to be '0' outside the contour and '1' inside the contour, each levelset may be presented as simply a two-dimensional binary image. To facilitate ease of computation, to determine the mean and variance of the contour data, the two-dimensional binary image of each levelset may be serialized and converted to a vector.

Then, calculation of the mean of the contour data for the past iterations may involve calculating a mean vector for the converted levelsets. Once the mean vector is calculated, the variance of the same contour data may be calculated. However, this may not be as straightforward as calculating the variance of a set scalar data values. To calculate the variance of the contour data, in some embodiments, it may be necessary to calculate the covariance matrix of the set of vectors that were converted from the past levelsets. The trace of the covariance matrix may then intuitively be considered the vector equivalent of a standard deviation value for a set of scalar values.

In act 314, the mean and variance of the contour data is determined for a number of past iterations. This number can be any suitable number that is sufficiently high to capture a large enough number of past iterations for determining convergence in the contour identification process. For example, in various embodiments, the predetermined number of past iterations is at least seven (7). In a particular example embodiment, the number of past iterations is ten (10).

Referring still to FIG. 3A, at act 316, there may be a determination of whether the variance of the contour data relative to the mean of the contour data is less than a threshold. In the example embodiment where the mean is provided as a mean vector, and the variance is determined as the trace of a covariance matrix, act 316 may be performed by dividing the trace of the covariance by the norm of the mean vector.

At act 318, if the result of act 316 is not less than the given threshold (the 'NO' branch of act 318), then the contour identification process may continue to the next iteration (e.g., continuing to evolve the levelset function to dilate the contour) and the method may proceed back to act 314 to repeat determining whether the convergence parameter has been achieved.

If it is determined that the result of act 316 is less than a given threshold (the 'YES' branch of act 318), the method may proceed to act 320 and the convergence parameter may be considered achieved and the contour identified (subject to optional adjustment in act 322 discussed below). In various embodiments, this threshold may be set to a percentage. For example, in some embodiments, the threshold may be between three (3) and twenty (20) percent. In a particular example embodiment, the threshold may be five (5) percent. After act 320, the method may proceed to act 322.

Act 322 involves displaying a user interface control on the touchscreen device that, when activated, adjusts the identified contour to contract the contour or further dilate the contour. This user interface control is not shown in FIGS. 2A-2B. However, in an example embodiment, the user interface control may be a slider control that when adjusted to one side, continues to iterate the contour identification process and expand the contour using the dilation morphological operator of the contour identification process; and when adjusted to the other side, displays a contraction of the contour. The displaying of the contraction of the contour may be performed in various ways. For example, the user interface may simply display the last iteration(s) of the contour identification process already stored in memory (e.g., as may be stored for determining whether a convergence parameter has been achieved, as discussed above). Additionally or alternatively, the contraction of the contour may be performed by continuing to execute the contour identification process, but with the morphological operator modified to use an erosion operator to contract the contour instead of a dilation operator to grow the contour. Any type of suitable user control may be used for this purpose at act 322. For example, the user interface control may be a dial control, and/or a switch control.

This type of user interface control may allow fine-tuning of the contour identified by the contour identification process. This may be desirable because the identified contour (e.g., as a result of determining that the convergence parameter has been achieved or otherwise) may not reflect the underlying structure in the ultrasound image as accurately as the ultrasound operator desires. Providing a user interface control of this nature may thus provide the benefit of automated contour identification process, while still providing the ultrasound operator with the precise control they may desire to fine-tune any identified contour. In embodiments where the contraction of the contour is performed by simply displaying past iterations (e.g., past levelsets) of the contour identification process, the storage of the past iterations may thus serve at least two purposes: for determination of whether the convergence parameter has been achieved, and also to allow for ease of displaying the contraction of the contour. After adjustment using the user interface control of act 322, the adjusted contour may be considered the identified contour.

The user interface control of act 322 has generally been discussed above with respect to adjusting the identified contour (e.g., contracting or expanding the contour). However, in various embodiments, an analogous user interface control may be provided to allow adjustment of other parameters of the contour identification process such as the smoothness (e.g., the amount of jaggedness) of the boarders of the contour.

After act 322, the method may proceed to act 130' on FIG. 3B. At act 130', upon identification of a contour from the contour identification process, measurement calipers may be placed on the identified contour. An analogous act 130 in FIG. 1 was discussed above, in reference to frame '8' in FIG. 2B. However, the above discussion did not indicate how the positioning of the calipers is determined. Acts 332-336 of FIG. 3B discusses how this may be performed in an example embodiment.

Act 332 may involve determining an axis of the identified contour. In some example embodiments, the methods described herein may be performed on ultrasound images of bladders or ovarian follicles. In these images, these types of anatomy are generally in an oblong shape that has a major (longer) axis and a minor (shorter) axis. Referring again simultaneously to frame '8' of FIG. 2B, the major axis is illustrated there horizontally, and the minor axis is illustrated vertically. These axes may be determined in various ways. For example, principal component analysis may be used to determine one or more of these axes. Additionally or alternatively, independent component analysis may be used. Once the axes have been determined, the method may proceed to act 334.

At act 334, a length of one or more of the identified axes may be extended so that ends of the length overlap with contour. For example, this may be desirable in cases where an axis determined at act 332 do not fully coincide with an edge of the identified contour.

At act 336, the calipers may then be placed on the ends of the length of the axis. As noted, an example screenshot of placed calipers is shown in frame '8' of FIG. 2B. The calipers are shown in green color.

In some embodiments, prior to the storing of the value identified by the measurement calipers, the method further optionally perform act 338. Act 338 may involve receiving, via the touchscreen device, second input coordinates on the ultrasound image, the second input coordinates adjusting at least one side of the measurement calipers displayed on the identified contour. Referring simultaneously to frame '9' of FIG. 2B, shown there on ultrasound image 218 is an example user interface that may allow for receiving of second input coordinates to adjust at least one side of the measurement calipers. As shown in FIG. 2B, the user interface shows circles in purple color for where the second input coordinates can be inputted to adjust the calipers placed by the methods described herein. Input may be received via these user interface controls to lengthen or shorten the caliper (e.g., so as to correspondingly increase or decrease the associated measurement).

The input received at act 338 need not be provided in the form shown in frame '9' of FIG. 2B, and other ways user interface methods may be possible. For example, in some embodiments, a user interface control similar to what was discussed above with respect to act 322 may be displayed (e.g., a slider or dial control), and this control may be used to adjust the caliper that is placed at act 336 of FIG. 3B and/or 130' of FIG. 1. For example, for a slider control, when input is received to move the slider to one side, the caliper may lengthen; and when input is received to move the slider to the other side, the caliper may shorten.

Similar to the user interface control discussed above for act 322, a user interface control to adjust the automatically-placed calipers may allow an ultrasound operator to fine-tune the caliper that is placed by the methods described herein. This may allow the ultrasound operator to have the precise control over placement of the caliper when desired, while still providing the ease-of-use with the automatic caliper placement in most situations.

Referring back to FIG. 3B, at act 140', the method may proceed to store a value identified by the measurement calipers as the measurement. This may be performed in a manner similar to act 140 discussed above with respect to FIG. 1.

Figure 4:
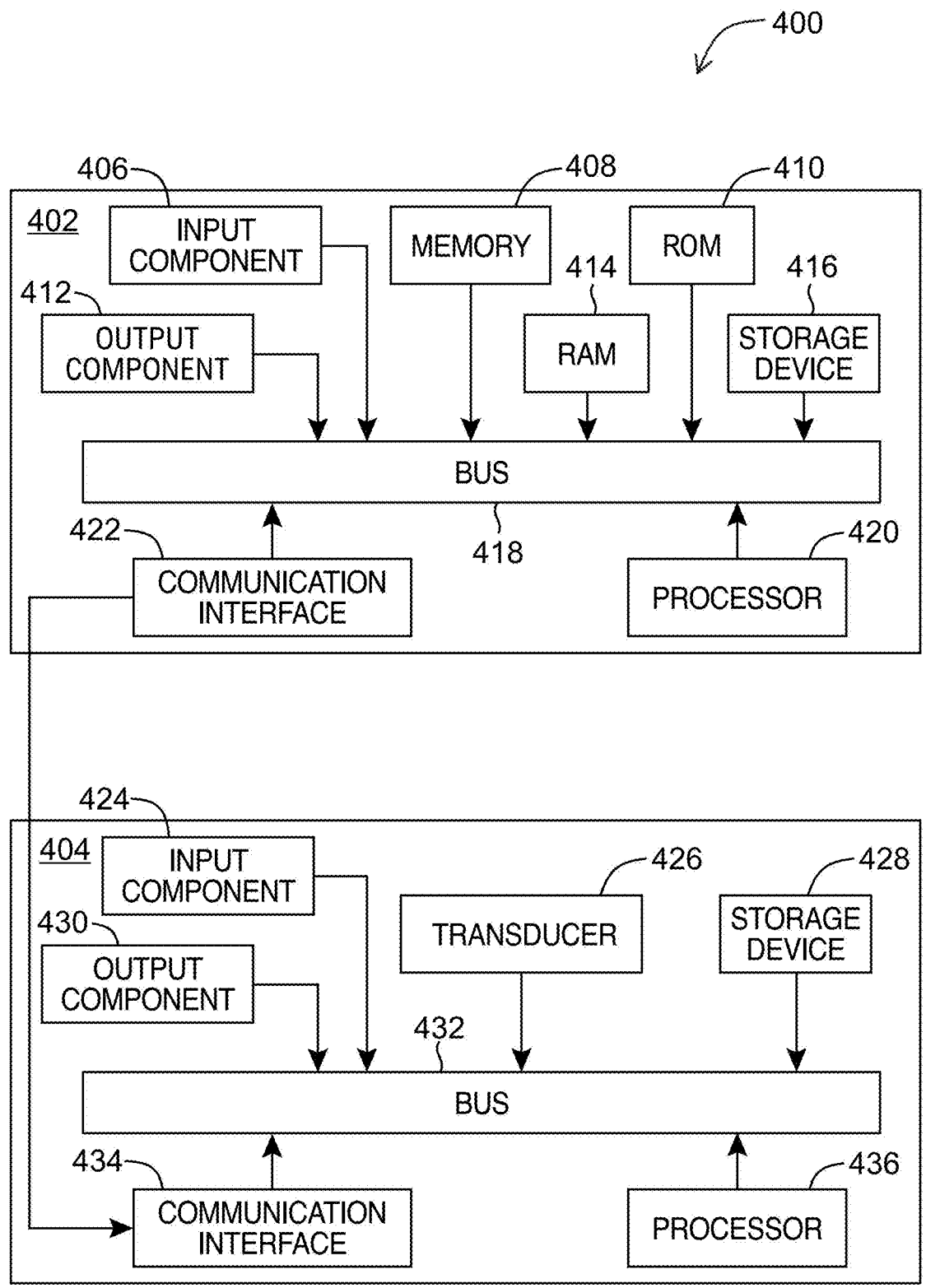
FIG. 4 shows a functional block diagram of an ultrasound system, in accordance with at least one embodiment of the present invention.

Referring to FIG. 4, shown there generally as 400 is a functional block diagram of an ultrasound system and/or apparatus, in accordance with at least one embodiment of the present invention. For example, one or more components of the ultrasound imaging system 400 may be configured to perform the methods of FIGS. 1 and/or 3A-3B to perform a measurement on an ultrasound image displayed on a touch-screen device.

Ultrasound imaging system 400 may include an ultrasound acquisition unit 404 configured to transmit ultrasound energy to a target object, receive ultrasound energy reflected from the target object, and generate ultrasound image data based on the reflected ultrasound energy. The ultrasound acquisition unit 404 may include a transducer 426 which converts electric current into ultrasound energy and vice versa. Transducer 426 may transmit ultrasound energy to the target object which echoes off the tissue. The echoes may be detected by a sensor in transducer 426 and relayed through a bus 432 to a processor 436. Processor 436 may interpret and process the echoes to generate image data of the scanned tissue. In some embodiments, the ultrasound acquisition unit 404 (or various components thereof) may be provided as a handheld ultrasound probe or scanner that is in communication with other components of the ultrasound imaging system 400. For example, the handheld probe may include the transducer 426 of ultrasound acquisition unit 404. Ultrasound acquisition unit 404 may also include storage device 428 (e.g., a computer readable medium, coupled to and accessible by bus 432) for storing software or firmware instructions, configuration settings (e.g., sequence tables), and/or ultrasound image data.

Although not illustrated, as will be apparent to one of skill in the art, the ultrasound imaging system 400 may include other components for acquiring, processing and/or displaying ultrasound image data. These include, but are not limited to: a scan generator, transmit beamformer, pulse generator, amplifier, analogue to digital converter (ADC), receive beamformer, signal processor, data compressor, wireless transceiver and/or image processor. Each of these may be components of ultrasound acquisition unit 404 and/or electronic display unit 402 (described below).

Ultrasound imaging system 400 may include an electronic display unit 402 which is in communication with ultrasound acquisition unit 404 via communication interfaces 422/434. In various embodiments, communication interfaces 422/434 may allow for wired or wireless connectivity (e.g., via Wi-Fi™ and/or Bluetooth™) between the electronic display unit 402 and the ultrasound acquisition unit 404. Electronic display unit 402 may work in conjunction with ultrasound acquisition unit 404 to control the operation of ultrasound acquisition unit 404 and display the images acquired by the ultrasound acquisition unit 404. An ultrasound operator may interact with the user interface provided by display unit 402 to send control commands to the ultrasound acquisition unit 404 (e.g., to change presets for acquiring a bladder or ovarian follicle image). The electronic display unit 402 may have been referred to as a multi-use display device, a touchscreen device, and/or a mobile device above. In various embodiments, the electronic display unit 402 may be a portable device, which may include a mobile device (e.g. smartphone), tablet, laptop, or other suitable device incorporating a display and a processor and capable of accepting input from a user and processing and relaying the input to control the operation of the ultrasound acquisition unit 404 as described herein.

Each of ultrasound acquisition unit 404 and display unit 402 may have one or more input components 424, 406 and/or one or more output components 430, 412. In the FIG. 4 embodiment, ultrasound acquisition unit 404 may include an input component 424 which is configured to accept input from the user (e.g., a user-programmable button for adjusting imaging parameters; and/or circuitry to turn on the ultrasound acquisition unit 404 and/or control the connection of the ultrasound acquisition unit 404 to the electronic display unit 402). For example, in some embodiments, ultrasound acquisition unit 404 may also include an output component 430, such as a LED indicator light which can output the status of the ultrasound acquisition unit 404.

In the FIG. 4 embodiment, display unit 402 may include an input component 406 configured to accept input from the user. Certain input received at input component 406 may be relayed to ultrasound acquisition unit 404 to control the operation of ultrasound acquisition unit 404. Display unit 402 may also include an output component 412, such as a display screen, which displays images based on image data acquired by ultrasound acquisition unit 404. In particular embodiments, display unit 402's input component 406 may include a touch interface layered on top of the display screen of the output component 412, so as to provide a touchscreen interface. Electronic display unit 402 may also include memory 408, Random Access Memory (RAM) 414, Read Only Memory (ROM) 410, and persistent storage device 416, which may all be connected to bus 418 to allow for communication therebetween and with processor 420. Any number of these memory elements may store software or firmware that may be accessed and executed by processor 420 to perform the acts of the methods described herein (e.g., so that the processor 420 is configured to perform the methods described herein of performing a measurement on an ultrasound image displayed on a touchscreen device).

In various embodiments, at least a portion of the processing of the image data corresponding to the reflected ultrasound energy detected by the transducer 426 may be performed by one or more of processors internal to the ultrasound acquisition unit 404 (such as by the processor 436) and/or by processors external to the ultrasound acquisition unit 404 (such as the processor 420 of electronic display unit 402).

Scan conversion is a process that converts image data to allow it to be displayed in a form that is more suitable for human visual consumption. For example, this may involve converting the image data from the data space (e.g. polar coordinate form) to the display space (e.g. Cartesian coordinate form). In an example embodiment, the ultrasound acquisition unit 404 may provide pre-scan-converted data to the electronic display unit 402, and the electronic display unit 402 may proceed to scan convert the data. The methods described herein then generally be performed on the post-scan-converted data at display unit 402 with a touchscreen device.

In some embodiments, the ultrasound acquisition unit 404 may have a lightweight, portable design and construction (e.g., when it is a handheld probe). In particular embodiments, the handheld probe may have a mass that is less than approximately 1 kg (2 lbs).

In some embodiments, all the input controls and display screen necessary for the operation of the ultrasound imaging system 400 may be provided by input and output components 406, 412 of the display unit 402. In such cases input and output components 424, 430 of ultrasound acquisition unit 404 may be optional and/or omitted. As noted, in certain embodiments, the ultrasound acquisition unit 404 may be a handheld probe (e.g., including transducer 426) which is in communication with the display unit 402 over the communications interfaces 422/434 to facilitate operation of the ultrasound acquisition unit 404 and processing and display of ultrasound images.

In some embodiments, the output component 430 of ultrasound acquisition unit 404 may include a display screen, which can be configured to display or otherwise output the images acquired by ultrasound acquisition unit 404 (in addition to or alternative to displaying such images on the display unit 402).

While a number of exemplary aspects and embodiments have been discussed above, those of skill in the art will recognize that may be certain modifications, permutations, additions and sub-combinations thereof. While the above description contains many details of example embodiments, these should not be construed as essential limitations on the scope of any embodiment. Many other ramifications and variations are possible within the teachings of the various embodiments.

INTERPRETATION OF TERMS

Unless the context clearly requires otherwise, throughout the description and the claims:
"comprise", "comprising", and the like are to be construed in an inclusive sense, as opposed to an exclusive or exhaustive sense; that is to say, in the sense of "including, but not limited to";
"connected", "coupled", or any variant thereof, means any connection or coupling, either direct or indirect, between two or more elements; the coupling or connection between the elements can be physical, logical, or a combination thereof;
"herein", "above", "below", and words of similar import, when used to describe this specification, shall refer to this specification as a whole, and not to any particular portions of this specification;
"or", in reference to a list of two or more items, covers all of the following interpretations of the word: any of the items in the list, all of the items in the list, and any combination of the items in the list;
the singular forms "a", "an", and "the" also include the meaning of any appropriate plural forms.

Unless the context clearly requires otherwise, throughout the description and the claims:
Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples but should be given the broadest interpretation consistent with the description as a whole.

What is claimed is:

1. A method for performing a measurement on an ultrasound image displayed on a touchscreen device, the method comprising:
receiving, via the touchscreen device, first input coordinates corresponding to a point on the ultrasound image;
using the first input coordinates as a seed for performing a contour identification process on the ultrasound image, wherein the contour identification process performs contour evolution using morphological operators to iteratively dilate from the first input coordinates until a convergence parameter is achieved, wherein determining whether the convergence parameter is achieved comprises:
for a predetermined number of past iterations of the contour identification process, determining a mean and a variance of the contour data for the predetermined number of past iterations;
determining if the variance of the contour data relative to the mean of the contour data is less than a threshold; and
if the variance of the contour data relative to the mean is determined to be less than the threshold, the convergence parameter is determined to be achieved;
upon identification of a contour from the contour identification process, placing measurement calipers on the identified contour; and
storing a value identified by the measurement calipers as the measurement.

2. The method of claim 1, wherein prior to the storing of the value identified by the measurement calipers, the method further comprises:
receiving, via the touchscreen device, second input coordinates on the ultrasound image, wherein the second input coordinates adjust at least one side of the measurement calipers displayed on the identified contour.

3. The method of claim 1, wherein when placing the calipers on the identified contour, the method further comprises:
determining an axis of the identified contour;
extending a length of the axis so that ends of the length overlap with contour; and
placing the calipers on the ends of the length.

4. The method of claim 3, wherein principal component analysis is used to determine the axis of the identified contour, and wherein the axis is a major axis or a minor axis identified by the principal component analysis.

5. The method of claim 1, wherein the predetermined number of past iterations is at least 7.

6. The method of claim 1, wherein each past iteration of the contour identification process comprises a levelset, and wherein the determining the mean and the variance of the contour data for the predetermined number of past iterations further comprises:
for each levelset, converting the levelset to a vector by serializing the two-dimensional data of the levelset;
calculating a mean vector for the converted levelsets, to determine the mean of the contour data for the predetermined number of past iterations; and
calculating the trace of the covariance of the converted levelsets, to determine the variance of the contour data for the predetermined number of past iterations.

7. The method of claim 6, wherein the determining if the variance of the contour data relative to the mean of the contour data is less than the threshold comprises dividing the trace of the covariance of the converted levelsets by the norm of the mean vector.

8. The method of claim 7, wherein the threshold is between 3 and 20 percent.

9. The method of claim 1, wherein after the convergence parameter is achieved, the method further comprises:
displaying a user interface control on the touchscreen device that, when activated, adjusts the identified contour to contract the contour or further dilate the contour.

10. The method of claim 1, wherein the convergence parameter comprises a maximum number of iterations, and the determining whether the convergence parameter is achieved further comprises determining if the contour identification process is executed for the maximum number of iterations.

11. A touchscreen device capable of communicating with an ultrasound acquisition unit, the touchscreen device comprising:
a processor; and
a memory storing instructions for execution by the processor, the instructions for performing a measurement on an ultrasound image displayed on a touchscreen device, wherein when the instructions are executed by the processor, the processor is configured to:
receive, via the touchscreen device, first input coordinates corresponding to a point on the ultrasound image;
use the first input coordinates as a seed for performing a contour identification process on the ultrasound image, wherein the contour identification process performs contour evolution using morphological operators to iteratively dilate from the first input coordinates until a convergence parameter is achieved, wherein to determine whether the convergence parameter is achieved, the processor is further configured to:
for a predetermined number of past iterations of the contour identification process, determine a mean and a variance of the contour data for the predetermined number of past iterations;
determine if the variance of the contour data relative to the mean of the contour data is less than a threshold; and
if the variance of the contour data relative to the mean is determined to be less than the threshold, the convergence parameter is determined to be achieved;
upon identification of a contour from the contour identification process, place measurement calipers on the identified contour; and
store a value identified by the measurement calipers as the measurement.

12. The touchscreen device of claim 11, wherein when placing the calipers on the identified contour, the processor is further configured to:
determine an axis of the identified contour;
extend a length of the axis so that ends of the length overlap with contour; and
place the calipers on the ends of the length.

13. The touchscreen device of claim 11, wherein each past iteration of the contour identification process comprises a levelset, and wherein when determining the mean and the variance of the contour data for the predetermined number of past iterations, the processor is further configured to:
for each levelset, convert the levelset to a vector by serializing the two-dimensional data of the levelset;
calculate a mean vector for the converted levelsets, to determine the mean of the contour data for the predetermined number of past iterations; and calculate the trace of the covariance of the converted levelsets, to determine the variance of the contour data for the predetermined number of past iterations.

14. The touchscreen device of claim 13, wherein when determining if the variance of the contour data relative to the mean of the contour data is less than the threshold, the processor is further configured to divide the trace of the covariance of the converted levelsets by the norm of the mean vector.

15. The touchscreen device of claim 14, wherein the threshold is between 3 and 20 percent.

16. The touchscreen device of claim 11, wherein after the convergence parameter is achieved, the processor is further configured to:
  display a user interface control on the touchscreen device that, when activated, adjusts the identified contour to contract the contour or further dilate the contour.

17. The touchscreen device of claim 11, wherein prior to storing of the value identified by the measurement calipers, the processor is further configured to:
  receive, via the touchscreen device, second input coordinates on the ultrasound image, wherein the second input coordinates adjust at least one side of the measurement calipers displayed on the identified contour.

18. The touchscreen device of claim 11, wherein the predetermined number of past iterations is at least 7.

19. The touchscreen device of claim 11, wherein the convergence parameter comprises a maximum number of iterations, and to determine whether the convergence parameter is achieved, the processor is further configured to determine if the contour identification process is executed for the maximum number of iterations.

20. A non-transitory computer readable medium storing instructions for performing a measurement on an ultrasound image displayed on a touchscreen device, the instructions for execution by a processor of a touchscreen device, wherein when the instructions are executed by the processor, the processor is configured to:
  receive first input coordinates corresponding to a point on the ultrasound image;
  use the first input coordinates as a seed for performing a contour identification process on the ultrasound image, wherein the contour identification process performs contour evolution using morphological operators to iteratively dilate from the first input coordinates until a convergence parameter is achieved, wherein to determine whether the convergence parameter is achieved, the processor is further configured to:
    for a predetermined number of past iterations of the contour identification process, determine a mean and a variance of the contour data for the predetermined number of past iterations;
    determine if the variance of the contour data relative to the mean of the contour data is less than a threshold; and
    if the variance of the contour data relative to the mean is determined to be less than the threshold, the convergence parameter is determined to be achieved;
  upon identification of a contour from the contour identification process, place measurement calipers on the identified contour; and
  store a value identified by the measurement calipers as the measurement.

* * * * *